United States Patent
Shin et al.

(10) Patent No.: US 10,723,696 B2
(45) Date of Patent: Jul. 28, 2020

(54) XYLYLENE DIISOCYANATE COMPOSITION WITH IMPROVED STABILITY AND REACTIVITY AND OPTICAL LENS USING THE SAME

(71) Applicant: SKC CO., LTD., Suwon-si, Gyeonggi-do (KR)

(72) Inventors: Junghwan Shin, Suwon-si (KR); Hyuk Hee Han, Seongnam-si (KR); Seung Mo Hong, Incheon (KR); Sang Mook Kim, Ulsan (KR)

(73) Assignee: SKC CO., LTD., Suwon-si (KR)

( * ) Notice: Subject to any disclaimer, the term of this patent is extended or adjusted under 35 U.S.C. 154(b) by 72 days.

(21) Appl. No.: 15/980,821

(22) Filed: May 16, 2018

(65) Prior Publication Data
US 2018/0334428 A1 Nov. 22, 2018

(30) Foreign Application Priority Data

May 17, 2017 (KR) .................. 10-2017-0061073

(51) Int. Cl.
| | | |
|---|---|---|
| *C08G 18/00* | (2006.01) |
| *C07C 263/18* | (2006.01) |
| *C08G 18/76* | (2006.01) |
| *G02B 1/04* | (2006.01) |
| *C07C 263/20* | (2006.01) |
| *C08G 18/38* | (2006.01) |
| *C07C 265/08* | (2006.01) |
| *C07C 265/14* | (2006.01) |

(52) U.S. Cl.
CPC .......... *C07C 263/18* (2013.01); *C07C 263/20* (2013.01); *C07C 265/08* (2013.01); *C07C 265/14* (2013.01); *C08G 18/3868* (2013.01); *C08G 18/3876* (2013.01); *C08G 18/7642* (2013.01); *G02B 1/04* (2013.01); *G02B 1/041* (2013.01)

(58) Field of Classification Search
CPC ... C07C 263/18; C07C 263/20; C07C 265/14; C07C 265/08; C08G 18/3868; C08G 18/7642; G02B 1/041
USPC .................... 528/77, 76, 44; 520/1
See application file for complete search history.

(56) References Cited

U.S. PATENT DOCUMENTS

| | | | |
|---|---|---|---|
| 3,658,656 A * | 4/1972 | Adica | C07C 263/20 203/49 |
| 3,660,456 A | 5/1972 | Naito et al. | |
| 5,302,749 A * | 4/1994 | Nagata | C07C 263/18 560/333 |
| 5,364,897 A | 11/1994 | Knight et al. | |
| 5,576,412 A | 11/1996 | Hirata et al. | |
| 2009/0124785 A1 | 5/2009 | Shimakawa et al. | |
| 2013/0303721 A1 | 11/2013 | Jang et al. | |
| 2018/0334428 A1 | 11/2018 | Shin et al. | |

FOREIGN PATENT DOCUMENTS

| | | |
|---|---|---|
| GB | 1254690 A | 11/1971 |
| JP | 5-78304 A | 3/1993 |
| JP | 7-33851 A | 2/1995 |
| JP | 3091979 B2 | 9/2000 |
| JP | 2014-234429 A | 12/2014 |
| KR | 1992-0021658 A | 12/1992 |
| KR | 10-2012-0076329 A | 7/2012 |
| KR | 10-1842254 B1 | 3/2018 |
| WO | 2007/010996 A1 | 1/2007 |
| WO | 2017/148795 A1 | 9/2017 |

OTHER PUBLICATIONS

The Korea Intellectual Property Office; Communication dated Dec. 18, 2018 in counterpart KR application No. 10-2017-0165811.
European Patent Office; Communication dated Aug. 7, 2018 in counterpart EP application No. 18170216.8.

* cited by examiner

*Primary Examiner* — Jessica Whiteley
(74) *Attorney, Agent, or Firm* — Sughrue Mion, PLLC

(57) ABSTRACT

The xylylene diisocyanate composition according to the embodiments has a chlorine content of 100 to 1,000 ppm to improve the stability, so that the degradation of the reactivity can be prevented even when it is stored for a long period of time. Therefore, even if the xylylene diisocyanate composition according to the embodiments is used after it has been stored for a long period of time for sale or the like, the xylylene diisocyanate composition can be polymerized with a thiol to produce a polythiourethane-based optical material having excellent properties such as refractive index, Abbe number, transparency, glass transition temperature, yellowness index, and the like. Therefore, it can be advantageously used in the field of eyeglass lenses, camera lenses, and the like.

16 Claims, No Drawings

XYLYLENE DIISOCYANATE COMPOSITION WITH IMPROVED STABILITY AND REACTIVITY AND OPTICAL LENS USING THE SAME

TECHNICAL FIELD

Embodiments relate to a xylylene diisocyanate composition used in the production of an optical material, more specifically a xylylene diisocyanate composition having improved stability and reactivity, and an optical material such as a plastic optical lens using the same.

BACKGROUND ART

Since plastics optical materials are lightweight, hardly breakable, and excellent in dyeability as compared with optical materials made of inorganic materials such as glass, they are widely used as optical materials for eyeglass lenses, camera lenses, and the like. Recently, there has been a demand for high performance of optical materials having such properties as a high transparency, a high refractive index, a low specific gravity, a high heat resistance, and a high impact resistance.

Polythiourethanes among the optical materials are widely used as an optical material by virtue of their excellent optical properties and excellent mechanical properties. Polythiourethanes may be prepared by reacting a thiol and an isocyanate. Lenses produced from polythiourethanes are widely used since they have a high refractive index, a lightweight, and a relatively high impact resistance.

Xylylene diisocyanate among the isocyanates used as a raw material of a polythiourethane is generally synthesized from xylylenediamine by a phosgene method or a non-phosgene method and is commercially used in a very wide range of fields.

Although xylylene diisocyanate has various advantages, it also has disadvantages in that it is difficult for a product produced therefrom to have uniform characteristics because of the high reactivity of the NCO groups and that it is liable to lose its original physical properties due to side reactions when it is stored for a long period of time. Specifically, xylylene diisocyanate forms a dimer or a trimer due to the self-reaction of the NCO groups, thereby changing its NCO % value. As a result, a solid material is precipitated, and this phenomenon is further accelerated by the reaction with moisture introduced from the environment. Various stabilizers may be used to prevent or retard such problems, but this may cause yellowing or other problems in the production of polyurethanes as they affect the reactivity of xylylene diisocyanate. Furthermore, unlike other types of isocyanates, xylylene diisocyanate has a much greater side effect depending on the kind and content of additives, which makes it difficult to find an optimal formulation.

PRIOR ART DOCUMENT

Patent Document (Patent document 1) Korean Laid-open Patent Publication No. 2012-0076329 (Jul. 9, 2012)

DISCLOSURE OF INVENTION

Technical Problem

When xylylene diisocyanate is used in the production of an optical material, various kinds of side reactions may take place due to its high reactivity, which may generate a solid material and have a serious impact on the optical characteristics of the optical material. In order to resolve this problem, attempts have been made to reduce the impurities in xylylene diisocyanate, which may affect the reactivity, to a very minute amount. However, it is commercially very difficult to reduce the amount of impurities to the maximum, and it also incurs a large amount of expenses to operate such process.

As a result of researches, the inventors of the present invention have found that if a xylylene diisocyanate composition contains a certain amount of chlorine, it may improve the stability and prevents the degradation of the reactivity.

Accordingly, the embodiments aim to provide a xylylene diisocyanate composition having improved stability and reactivity by adjusting the amount of chlorine to a specific range, and a process for preparing the same.

Also, the embodiments aim to provide a storage article of a xylylene diisocyanate composition, which is stable even when stored for a long period of time.

In addition, the embodiments aim to provide a polymerizable composition using the xylylene diisocyanate composition, an optical material, and a process for producing a plastic optical lens.

Solution to Problem

According to an embodiment, there is provided a xylylene diisocyanate composition, which has a chlorine content of 100 to 1,000 ppm and a content of NCO groups of 43 to 46% by weight.

According to another embodiment, there is provided a xylylene diisocyanate composition, which comprises xylylene diisocyanate having a content of NCO groups of 43 to 46% by weight; and at least one of a chlorine ion and a chlorine-based storage stabilizer, wherein when the composition is sealed in a container that is not reactive with chlorine and left at a temperature of 80° C. for 6 months, the change in the content of NCO groups is within 4% as compared with the initial content.

Further, according to another embodiment, there is provided a process for preparing a xylylene diisocyanate composition, which comprises obtaining a first composition containing xylylene diisocyanate from xylylenediamine by an isocyanate synthesis process; and adding at least one of a chloride ion and a chlorine-based storage stabilizer to the first composition to adjust the chlorine content in the composition to 100 to 1,000 ppm.

Further, according to another embodiment, there is provided a storage article of a xylylene diisocyanate composition, which comprises a xylylene diisocyanate composition having a chlorine content of 100 to 1,000 ppm and a content of NCO groups of 43 to 46% by weight; and a container for containing the xylylene diisocyanate composition, wherein the regions of the container in contact with the xylylene diisocyanate composition are not reactive with chlorine.

Further, according to another embodiment, there is provided a polymerizable composition, which comprises a xylylene diisocyanate composition having a chlorine content of 100 to 1,000 ppm and a content of NCO groups of 43 to 46% by weight; and a thiol.

Further, according to another embodiment, there is provided an optical material, which comprises a polythiourethane prepared by polymerization of a xylylene diisocyanate composition having a chlorine content of 100 to 1,000 ppm and a content of NCO groups of 43 to 46% by weight and a thiol.

Further, according to another embodiment, there is provided a process for producing an optical lens, which comprises preparing a xylylene diisocyanate composition having a chlorine content of 100 to 1,000 ppm and a content of NCO groups of 43 to 46% by weight; and mixing the xylylene diisocyanate composition with a thiol and thermally curing the mixture in a mold.

Advantageous Effects of Invention

The xylylene diisocyanate composition according to the embodiments contains a certain amount of chlorine to improve the stability, so that the degradation of the reactivity can be prevented even when it is stored for a long period of time.

Therefore, even if the xylylene diisocyanate composition according to the embodiments is used after it has been stored for a long period of time for sale or the like, the xylylene diisocyanate composition can be polymerized with a thiol to produce a polythiourethane-based optical material having excellent properties in terms of refractive index, Abbe number, transparency, glass transition temperature, yellowness index, and the like. Therefore, it can be advantageously used in the field of eyeglass lenses, camera lenses, and the like.

DETAILED DESCRIPTION FOR CARRYING OUT THE INVENTION

Hereinafter, the present invention will be described in detail with reference to the examples. The examples are not limited to those described below. Rather, they may be modified into various forms as long as the gist of the invention is not altered.

In this specification, when a part is referred to as "comprising" an element, it is to be understood that the part may comprise other elements as well.

Further, all numbers and expression related to the quantities of components, reaction conditions, and the like used herein are to be understood as being modified by the term "about," unless otherwise indicated.

The xylylene diisocyanate composition according to an embodiment has a chlorine content of 100 to 1,000 ppm and a content of NCO groups of 43 to 46% by weight.

As described above, the xylylene diisocyanate composition has an adjusted amount of chlorine, which ranges from 100 to 1,000 ppm.

If the content of chlorine in the composition is less the above range, the high reactivity cannot be effectively restrained, so that cloudiness and precipitates may occur due to the self-reaction between the NCO groups when the composition is stored for a long period of time. If it exceeds the above range, it may cause yellowing due to an excessive amount of chlorine or a chlorine-based compound.

The chlorine content refers to the total amount of the chlorine ions and the chlorine components of the chlorine-based compounds contained in the xylylene diisocyanate composition, which may be measured by a method such as combustion ion chromatography.

In addition, the xylylene diisocyanate composition has a content of NCO groups (NCO %) of 43 to 46% by weight.

The above NCO content range is close to the theoretical NCO content in which the self-reaction between the NCO groups in xylylene diisocyanate would not take place. Within the above range, the physical properties of the xylylene diisocyanate composition according to the embodiment may not be deteriorated.

The content of NCO groups (NCO %) is a value converted from the weight in percent of the free NCO (reactive NCO) groups contained in the composition, which may be measured by a method such as back titration with hydrochloric acid.

As a more specific example, the chlorine content in the xylylene diisocyanate composition may range from 100 to 700 ppm.

The xylylene diisocyanate composition may comprise at least one of a chloride ion and a chlorine-based storage stabilizer.

For example, the xylylene diisocyanate composition may comprise at least one chlorine-based storage stabilizer represented by the following Formula 1 or 2:

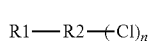
[Formula 1]

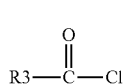
[Formula 2]

wherein n is an integer from 1 to 3; R1 is substituted or unsubstituted $C_{6-10}$ aryl; R2 is $C_{1-10}$ alkylene; and R3 is substituted or unsubstituted $C_{6-10}$ aryl or substituted or unsubstituted $C_{1-10}$ alkyl, and the groups substituted in the aryl and the alkyl may be each independently selected from the group consisting of halogen, hydroxy, amino, and the like.

As a specific example, the xylylene isocyanate composition may comprise at least one chlorine-based storage stabilizer selected from the group consisting of benzotrichloride (Formula 3), benzyl chloride (Formula 4), benzoyl chloride (Formula 5), and a $C_{1-10}$ alkanoyl chloride (Formula 6):

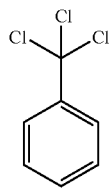
[Formula 4]

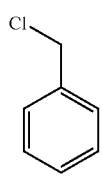
[Formula 5]

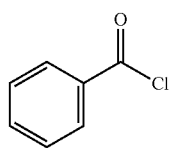
[Formula 6]

[Formula 7]

In the above Formula 7, R is $C_{1-10}$ alkyl.

The xylylene diisocyanate composition is very excellent in storage stability.

For example, when the xylylene diisocyanate composition is left at a temperature of 80° C. for 6 months, the amount of precipitates generated may be 1% by weight or less, 0.5% by weight or less, or 0.3% by weight or less, based on the total weight of the composition.

When the xylylene diisocyanate composition is left at a temperature of 80° C. for 6 months, the change in the NCO content may be within 5%, more preferably within 4%, within 3%, within 2%, or within 1%, as compared with the initial content.

Further, when the xylylene diisocyanate composition is sealed in a container that is not reactive with chlorine and left at a temperature of 80° C. for 6 months, the change in the NCO content may be within 4%, more preferably within 3%, within 2%, or within 1%, as compared with the initial content.

Accordingly, the xylylene diisocyanate composition according to an embodiment comprises xylylene diisocyanate having an NCO content of 43 to 46% by weight; and at least one of a chlorine ion and a chlorine-based storage stabilizer, wherein when the composition is sealed in a container that is not reactive with chlorine and left at a temperature of 80° C. for 6 months, the change in the NCO content is within 4% as compared with the initial content.

The amount of xylylene diisocyanate in the xylylene diisocyanate composition may be 90% by weight or more, 95% by weight or more, or 99% by weight or more, for example from 99% by weight to less than 100% by weight.

The process for preparing a xylylene diisocyanate composition according to an embodiment comprises obtaining a first composition containing xylylene diisocyanate from xylylenediamine by an isocyanate synthesis process; and adding at least one of a chloride ion and a chlorine-based storage stabilizer to the first composition to adjust the chlorine content in the composition to 100 to 1,000 ppm.

Hereinafter, each step will be described in detail.

In the step of obtaining the first composition, the composition containing xylylene diisocyanate is obtained from xylylenediamine by an isocyanate synthesis process (e.g., a phosgene method or a non-phosgene method).

For example, xylylenediamine may be reacted with phosgene, a halo $C_{1-10}$ alkyl chloroformate, or a halo di-$C_{1-10}$ alkyl carbonate to obtain the first composition containing xylylene diisocyanate.

According to an example of the phosgene method, as shown in Reaction Scheme 1 below, xylylenediamine may be reacted with hydrochloric acid at a temperature of 30° C. or lower in an ester-based solvent to obtain an amine hydrochloride, which may then be reacted with phosgene at 120 to 170° C., to thereby synthesize xylylene diisocyanate.

[Reaction Scheme 1]

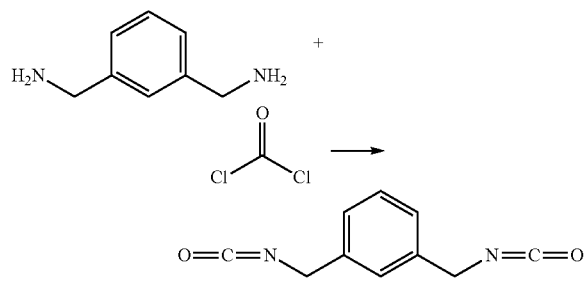

According to an example of the non-phosgene process, as shown in Reaction Scheme 2 below, xylylenediamine may be reacted with a halo $C_{1-10}$ alkyl chloroformate or a halo $C_{1-10}$ alkyl carbonate to prepare a biscarbamate, which may then be thermally decomposed in the presence of a catalyst at a high temperature of 130 to 250° C. in a solvent, to thereby synthesize xylylene diisocyanate.

[Reaction Scheme 2]

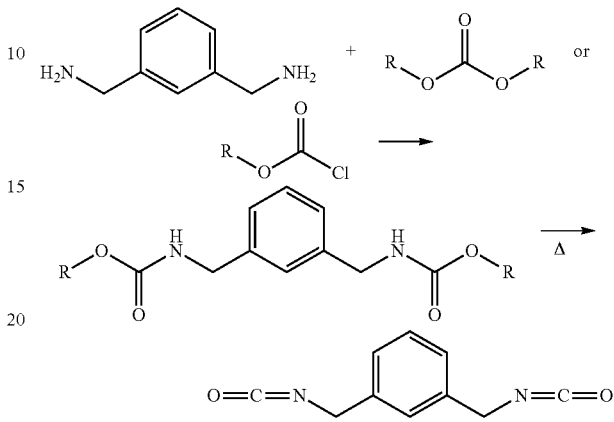

In the above Reaction Scheme 2, R is halo $C_{1-10}$ alkyl.

Here, the halo may be fluoro, chloro, bromo, or iodo.

According to the above method, the first composition containing xylylene diisocyanate is prepared. In such event, chlorine ions capable of hydrogenation are also produced in the phosgene method, while chlorine ions capable of hydrogenation are not produced in the non-phosgene method. Thus, it is necessary to deliberately adjust the chlorine content in the composition.

In the step of adjusting the chlorine content in the composition, the chlorine content in the first composition obtained in the preceding step is adjusted to 100 to 1,000 ppm.

The adjustment of the chlorine content may be carried out by adding at least one of a chloride ion and a chlorine-based storage stabilizer to the first composition.

For example, the step of adding a chlorine ion may be carried out by injecting and dissolving chlorine gas while the first composition is stirred at room temperature, and then removing the undissolved chlorine gas under a reduced pressure In addition, the step of adding a chlorine-based storage stabilizer may be carried out by adding at least one chlorine-based storage stabilizer to the first composition and stirring and mixing the mixture at 20 to 50° C. In such event, the chlorine-based storage stabilizer can be suitably used in a required amount of the compounds exemplified above. Preferably, the adjustment of the chlorine content may be carried out by adding to the first composition at least one chlorine-based storage stabilizer selected from the group consisting of benzotrichloride, benzyl chloride, benzoyl chloride, and a $C_{1-10}$ alkanoyl chloride.

In addition, if a chlorine ion or a chlorine-based compound is excessively present in, or added to, the first composition, a step of removing it may be further performed. That is, after the step of adjusting the chlorine content in the composition, a step may be further carried out in which the composition is subjected to heat distillation to remove the excess chlorine ion or chlorine-based compound present in the composition, to thereby adjust the chlorine content in the composition to 100 to 1,000 ppm.

Further, after each of the chlorine addition/removal steps, the chlorine content in the composition may be measured and, if necessary, these steps may be further carried out to adjust the chlorine content to 100 to 1,000 ppm.

The storage article of a xylylene diisocyanate composition according to an embodiment comprises a xylylene diisocyanate composition having a chlorine content of 100 to 1,000 ppm and a content of NCO groups of 43 to 46% by weight; and a container for containing the xylylene diisocyanate composition, wherein the regions of the container in contact with the xylylene diisocyanate composition are not reactive with chlorine.

In the case where the chlorine component in the xylylene diisocyanate composition is in contact with a reactive substance such as a metal, the concentration of impurities such as metal ions increases in the xylylene diisocyanate composition over time, and there is a risk of deterioration of the composition. Furthermore, it may have a serious impact on the reactivity of the composition and on the optical characteristics of lenses produced therefrom.

Therefore, the storage article according to the embodiment, which uses a container having contact regions that are not reactive with chlorine, can prevent elution of metal ions and the like due to the corrosion of the container.

For example, the regions of the container in contact with the xylylene diisocyanate composition may be made of a non-metal.

More specifically, the regions of the container in contact with the composition may be coated with at least one of a polymeric coating agent such as epoxy-based, polyethylene-based, fluorine-based (such as Teflon), silicone-based, phenol-based, alkyd-based, polyester-based, acrylic-based, amino-based, vinyl-based coating agents, and the like; or an inorganic metal coating agent such as molybdenum-based, phosphate-based, zinc-based coating agents, and the like.

Since the storage article as described above does not cause a reaction between the container and the composition, materials are hardly eluted from the container into the composition even if the composition is stored therein for a long period of time.

As a specific example, when the xylylene diisocyanate composition is sealed in the container and left at a temperature of 80° C. for 6 months, the change in the NCO content in the composition is within 4% as compared with the initial content, and the total amount of the materials (such as a metal) eluted from the container may be within 1 ppm, more preferably within 0.8 ppm, within 0.6 ppm, or within 0.4 ppm.

As another example, when the xylylene diisocyanate composition is sealed in the container and left at a temperature of 100° C. for 1 month, the change in the NCO content in the composition is within 4% as compared with the initial content, and the total amount of the materials (such as a metal) eluted from the container may be within 1 ppm, more preferably within 0.8 ppm, within 0.6 ppm, or within 0.4 ppm.

The polymerizable composition according to an embodiment comprises a xylylene diisocyanate composition having a chlorine content of 100 to 1,000 ppm and a content of NCO groups of 43 to 46% by weight; and a thiol.

The polymerizable composition may comprise the xylylene diisocyanate composition and the thiol in a mixed state or in a separated state.

That is, the xylylene diisocyanate composition and the thiol in the polymerizable composition may be in a state of being compounded in contact with each other or separated from each other so as not to contact each other.

In the polymerizable composition, the molar ratio of SH group/NCO group in the composition may be 0.5 to 3.0, more specifically 0.8 to 1.3.

The thiol may be a thiol oligomer or a polythiol and may be used alone or as a mixture of two or more thereof.

Specific examples of the thiol include 3,3'-thiobis[2-[(2-mercaptoethyl)thio]-1-propanethiol, bis(2-(2-mercaptoethylthio)-3-mercaptopropyl)sulfide, 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, bis(2-mercaptoethyl)sulfide, tetrakis(mercaptomethyl)methane, 2-(2-mercaptoethylthio)propane-1,3-dithiol, 2-(2,3-bis(2-mercaptoethylthio)propylthio)ethanethiol, bis(2,3-dimercaptopropanyl)sulfide, bis(2,3-dimercaptopropanyl)disulfide, 1,2-bis[(2-mercaptoethyl)thio]-3-mercaptopropane, 1,2-bis(2-(2-mercaptoethylthio)-3-mercaptopropylthio)ethane, 2-(2-mercaptoethylthio)-3-2-mercapto-3-[3-mercapto-2-(2-mercaptoethylthio)-propylthio]propylthio-propane-1-thiol, 2,2-bis-(3-mercaptopropionyloxymethyl)-butyl ester, 2-(2-mercaptoethy thio)-3-(2-(2-[3-mercapto-2-(2-mercaptoethylthio)-propylthio]ethylthio)ethylthio)propane-1-thiol, (4R,11S)-4,11-bismercaptomethyl-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio)propyl)thio)propylthiol)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), trimethylolpropane tris(3-mercaptopropionate), pentaerythritol tetrakis(2-mercaptoacetate), bispentaerythritol ether hexakis(3-mercaptopropionate), 1,1,3,3-tetrakis(mercaptomethylthio)propane, 1,1,2,2-tetrakis(mercaptomethylthio)ethane, 4,6-bis(mercaptoenylthio)-1,3-dithiane, pentaerythritol tetrakis(2-mercaptoacetate), pentaerythritol tetrakis(3-mercaptopropionate), 2-(2,2-bis(mercaptodimethylthio)ethyl)-1,3-dithiane, and the like.

The polymerizable composition may further comprise such additives as an internal mold release agent, an ultraviolet absorber, a polymerization initiator, a heat stabilizer, a color correcting agent, a chain extender, a crosslinking agent, a light stabilizer, an antioxidant, a filler, and the like.

The internal release agent may include a fluorine-based nonionic surfactant having a perfluoroalkyl group, a hydroxyalkyl group, or a phosphate ester group; a silicone-based nonionic surfactant having a dimethylpolysiloxane group, a hydroxyalkyl group, or a phosphate ester group; an alkyl quaternary ammonium salt such as trimethylcetylammonium salt, trimethylstearyl salt, dimethylethylcetylammonium salt, triethyldodecylammonium salt, trioctylmethylammonium salt, and diethylcyclohexadodecylammonium salt; and an acidic phosphate ester. It may be used alone or in combination of two or more thereof.

As the ultraviolet absorber, benzophenone-based, benzotriazole-based, salicylate-based, cyanoacrylate based, oxanilide-based, or the like may be used.

As the polymerization initiator, an amine-based, phosphorus-based, organosilicate-based, organic copper-based, organic gallium, organic zirconium, organic iron-based, organic zinc, organic aluminum, or the like may be used.

As the heat stabilizer, metal fatty acid salt-based, phosphorus-based, lead-based, organotin-based, or the like may be used alone or in combination of two or more thereof.

The optical material according to an embodiment comprises a polythiourethane prepared by polymerization of a xylylene diisocyanate composition having a chlorine content of 100 to 1,000 ppm and a content of NCO groups of 43 to 46% by weight and a thiol.

The polythiourethane as a raw material for the optical material according to the embodiment is prepared by polymerizing (and curing) the xylylene diisocyanate composition having a chlorine content adjusted as above and the thiol.

In such event, the molar ratio of SH group/NCO group in the polymerization reaction may be 0.5 to 3.0, more specifically 0.8 to 1.3.

Further, in order to control the reaction rate during the polymerization reaction, a reaction catalyst, which is usually used in the production of polyurethane, may be added. As the curing catalyst (or polymerization initiator), a tin-based catalyst may be used. For example, dibutyl tin dichloride, dibutyl tin dilaurate, dimethyl tin dichloride, or the like may be used.

More specifically, the optical material according to the embodiment may be produced by polymerizing (and curing) the xylylene diisocyanate composition in which the chlorine content is adjusted and the thiol, followed by molding thereof.

The optical material thus produced from the xylylene diisocyanate composition according to the embodiment has excellent optical properties. Therefore, the optical material can be advantageously used as a spectacle lens, a camera lens, or the like. The optical material may preferably be a polythiourethane-based lens, i.e., a plastic optical lens.

The process for producing an optical lens according to an embodiment comprises preparing a xylylene diisocyanate composition having a chlorine content of 100 to 1,000 ppm and a content of NCO groups of 43 to 46% by weight; and mixing the xylylene diisocyanate composition with a thiol and thermally curing the mixture in a mold.

In such event, the step of preparing the xylylene diisocyanate composition may comprise obtaining a composition containing xylylene diisocyanate from xylylenediamine by an isocyanate synthesis process; and adding at least one of a chloride ion and a chlorine-based storage stabilizer to the composition to adjust the chlorine content in the composition to 100 to 1,000 ppm.

In addition, the step of obtaining the composition and the step of adjusting the chlorine content in the composition may be carried out according to the same conditions and procedures as described above in the process for preparing a xylylene diisocyanate composition. If necessary, the step of heat distillation for removing excess chlorine as exemplified above may be further carried out.

Thereafter, the xylylene diisocyanate composition and the thiol are mixed and thermally cured in a mold. For this purpose, the xylylene diisocyanate composition is first mixed with the thiol to prepare a polymerizable composition. The polymerizable composition is degassed under a reduced pressure and then injected into a mold for molding an optical material. Such degassing and mold injection may be performed, for example, at a temperature range of 20 to 40° C.

Once the composition is injected into the mold, polymerization is usually carried out by gradually heating the composition from a low temperature to a high temperature. The polymerization temperature may be, for example, 30 to 150° C., particularly 40 to 130° C. In addition, a reaction catalyst, which is conventionally used in the production of polythiourethane, may be employed in order to control the reaction rate. Specific examples of the reaction catalyst are as exemplified above.

The polythiourethane-based optical material produced as a result is released from the mold to obtain a final optical lens.

The optical lens thus produced has an excellent glass transition temperature (Tg). For example, the optical lens may have a glass transition temperature (Tg) of 95° C. or greater, 100° C. or greater, 105° C. or greater, or 110° C. or greater, specifically in the range of 95 to 130° C., in the range of 100 to 130° C., or in the range of 105 to 125° C.

The optical lens thus produced is colorless and transparent and is excellent in such optical properties as refractive index and Abbe number.

The optical lens may have a refractive index in the range of 1.56 to 1.78 and more specifically in the range of 1.58 to 1.76, in the range of 1.60 to 1.78, in the range of 1.60 to 1.76, in the range of 1.65 to 1.75, or in the range of 1.69 to 1.75.

The optical lens may have an Abbe number of 20 or greater, and more specifically may be 30 or greater. For example, the optical lens may have an Abbe number in the range of 20 to 50, in the range of 25 to 50, in the range of 30 to 45, or in the range of 30 to 43.

The optical lens may have a light transmittance, for example, a light transmittance at a wavelength of 550 nm of 85.0% to 99.9%, more specifically 87.0% to 99.0% or 87.0% to 95.0%.

The optical lens may have a yellowness index (YI) of 25 or less, or 20 or less, and specifically may be in the range of 1 to 25, in the range of 1 to 20, in the range of 3 to 20, or in the range of 5 to 15.

In addition, the optical lens may have a glass transition temperature (Tg) of 90° C. or greater or 95° C. or greater, specifically in the range of 90 to 130° C., in the range of 95 to 120° C., or in the range of 95 to 115° C.

According to a preferred example, the optical lens may have a yellowness index (YI) of 1 to 20 and a light transmittance of 85 to 99% at a wavelength of 550 nm. Also, the optical lens may have an Abbe number of 30 to 45 and a glass transition temperature of 95 to 120° C.

Hereinafter, the present invention is explained in detail by Examples. The following Examples are intended to further illustrate the present invention, and the scope of the Examples is not limited thereto.

EXAMPLE

Example 1

Adjustment of the Chlorine Content in a Xylylene Diisocyanate Composition (1) Preparation of Raw Materials 15 parts by weight of m-xylylenamine was dissolved in 78 parts by weight of o-dichlorobenzene to prepare an amine solution. Thereafter, 44 parts by weight of phosgene was dissolved in 52 parts by weight of o-dichlorobenzene to prepare a solution, which was cooled to 10° C. with a brine condenser and then placed in a reaction vessel. The amine solution prepared above was slowly added thereto at a temperature of 50° C. or lower. At this time, the amount of the amine solution added was adjusted to 5 moles of phosgene per 1 mole of amine. Thereafter, the reaction vessel was sealed, and the reaction solution was stirred for 2 hours. After further reaction for 3 hours at a temperature of 140° C. and a pressure of 3 kg/cm$^2$, the hydrochloric acid gas produced during the reaction was discharged. Upon completion of the reaction, the excessive phosgene was removed by a distillation process. The product was purified by fractional distillation under a reduced pressure to produce an m-XDI composition.

(2) Adjustment of Chlorine Content

At least one of a chloride ion and a chlorine-based storage stabilizer was added to the m-XIDI composition obtained above to variously adjust the chlorine content.

In such event, the step of adding a chlorine ion was carried out by injecting chlorine gas while xylylene diisocyanate was stirred at room temperature for 1 hour to dissolve it, and then the undissolved chlorine gas was removed under a reduced pressure for about 30 minutes.

In addition, the step of adding a chlorine-based storage stabilizer was carried out by adding each of the chlorine-based storage stabilizers listed in Table 1 below, followed by sufficient stirring at 35° C. for about 1 hour.

Thereafter, the content of chlorine in the composition was measured by combustion ion chromatography. If excessive chlorine was present, the composition was subjected to distillation at 80° C. to remove the chlorine ion or chlorine-based compound. Then, the chlorine content was measured again; and, if necessary, the above steps were repeated. The final chlorine content in the composition is summarized in Table 1 below.

Test Example 1

Evaluation of Storage Stability of the Composition with Respect to the Chlorine Content The initial NCO content (NCO %) of the m-XDI compositions whose chlorine content had been adjusted in Example 1 was measured by a back titration method. First, an excess of n-butylamine relative to the theoretical NCO content was added and reacted, and the residual excessive n-butylamine was analyzed with a 0.1 N hydrochloric acid reagent. The results are shown in Table 1 below.

Table 1 also summarizes the initial color of the m-XDI compositions, whether cloudiness occurred, and whether precipitates were present. The cloudiness and precipitates were determined by placing the m-XDI composition into a clear glass bottle, filling the bottle with nitrogen, and sealing it, which was then allowed to stand for more than one day, and the appearance and the presence of submerged materials on the bottom were observed.

Thereafter, the m-XDI compositions were each stored at 80° C. for 6 months, and the NCO % of the m-XDI compositions were measured in the same manner as described above. The compositions were also observed with naked eyes for the color, cloudiness, and precipitates thereof. The results are shown in Table 1 below.

TABLE 1

|  |  | Chlorine | Initial value | | | | After 6 months (at 80° C.) | | | |
|---|---|---|---|---|---|---|---|---|---|---|
|  |  | (ppm) | NCO % | Color* | Cloudiness | Precipitate | NCO % | Color* | Cloudiness | Precipitate |
| m-XDI | Comp. 1 | 15 | 44.6 | T | X | X | 39.2 | T | ○ | ○ |
|  | Comp. 2 | 60 | 44.5 | T | X | X | 40.3 | T | ○ | ○ |
|  | Comp. 3 | 100 | 44.5 | T | X | X | 44.5 | T | X | X |
|  | Comp. 4 | 300 | 44.3 | T | X | X | 44.2 | T | X | X |
|  | Comp. 5 | 530 | 44.5 | T | X | X | 44.6 | T | X | X |
|  | Comp. 6 | 750 | 44.6 | T | X | X | 44.5 | T | X | X |
|  | Comp. 7 | 1,000 | 44.5 | T | X | X | 44.2 | T | X | X |
|  | Comp. 8 | 1,180 | 44.5 | T | X | X | 44.6 | Y | X | X |
|  | Comp. 9 | 1,400 | 44.3 | T | X | X | 44.2 | Y | X | X |
|  | Comp. 10 | 2,000 | 44.5 | T | X | X | 44.5 | Y | X | X |

*T: transparent; Y: changed to yellow

As confirmed from Table 1 above, the m-XDI compositions (compositions 3 to 7) having a chlorine content within 100 to 1,000 ppm retained a transparent color with almost no changes in the NCO % after storage for 6 months and without any cloudiness and precipitates. Thus, their stability was excellent even when they were stored for a long period of time.

In contrast, the other m-XDI compositions having a chlorine content of less than 100 ppm or more than 1,000 ppm changed to yellow or had cloudiness or precipitates after storage for 6 months, indicating decreased stability when they were stored for a long period of time.

Test Example 2

Evaluation of Storage Stability of the Compositions with Respect to the Container m-XDI compositions with various chlorine contents were prepared, and their initial concentrations of metal ions were measured. Then, they were each stored at 80° C. for 6 months in a container made of different materials, and the concentration of the residual metal ions was measured.

Table 2 shows the results of measurement of the samples stored in stainless steel (SUS 304) containers. Table 3 shows those of the samples stored in steel containers whose interior had been coated with polyethylene.

TABLE 2

Stored in stainless steel containers

|  |  | Chlorine | Initial value (ppm) | | | | After 6 months (at 80° C., ppm) | | | |
|---|---|---|---|---|---|---|---|---|---|---|
|  |  | (ppm) | Cr | Fe | Mn | Ni | Cr | Fe | Mn | Ni |
| m-XDI | Comp. 1 | 15 | <0.1 | <0.1 | <0.1 | <0.1 | <0.1 | <0.1 | <0.1 | <0.1 |
|  | Comp. 2 | 60 | <0.1 | <0.1 | <0.1 | <0.1 | <0.1 | 0.3 | <0.1 | <0.1 |
|  | Comp. 3 | 100 | <0.1 | <0.1 | <0.1 | <0.1 | <0.1 | 0.9 | <0.1 | <0.1 |
|  | Comp. 4 | 300 | <0.1 | <0.1 | <0.1 | <0.1 | <0.1 | 5.2 | <0.1 | 0.5 |
|  | Comp. 5 | 530 | <0.1 | <0.1 | <0.1 | <0.1 | 0.5 | 11 | 0.3 | 1.0 |
|  | Comp. 6 | 750 | <0.1 | <0.1 | <0.1 | <0.1 | 1.8 | 25 | 1.0 | 3.0 |
|  | Comp. 7 | 1,000 | <0.1 | <0.1 | <0.1 | <0.1 | 2.6 | 60 | 3.0 | 5.8 |
|  | Comp. 8 | 1,180 | <0.1 | <0.1 | <0.1 | <0.1 | 12 | 130 | 5.3 | 11 |
|  | Comp. 9 | 1,400 | <0.1 | <0.1 | <0.1 | <0.1 | 39 | 507 | 10 | 30 |
|  | Comp. 10 | 2,000 | <0.1 | <0.1 | <0.1 | <0.1 | 152 | 1550 | 120 | 160 |

TABLE 3

Stored in steel containers coated with polyethylene

|  |  | Chlorine | Initial value (ppm) | | | | After 6 months (at 80° C., ppm) | | | |
|---|---|---|---|---|---|---|---|---|---|---|
|  |  | (ppm) | Cr | Fe | Mn | Ni | Cr | Fe | Mn | Ni |
| m-XDI | Comp. 1 | 15 | <0.1 | <0.1 | <0.1 | <0.1 | <0.1 | <0.1 | <0.1 | <0.1 |
|  | Comp. 2 | 60 | <0.1 | <0.1 | <0.1 | <0.1 | <0.1 | <0.1 | <0.1 | <0.1 |
|  | Comp. 3 | 100 | <0.1 | <0.1 | <0.1 | <0.1 | <0.1 | <0.1 | <0.1 | <0.1 |
|  | Comp. 4 | 300 | <0.1 | <0.1 | <0.1 | <0.1 | <0.1 | <0.1 | <0.1 | <0.1 |
|  | Comp. 5 | 530 | <0.1 | <0.1 | <0.1 | <0.1 | <0.1 | <0.1 | <0.1 | <0.1 |
|  | Comp. 6 | 750 | <0.1 | <0.1 | <0.1 | <0.1 | <0.1 | <0.1 | <0.1 | <0.1 |
|  | Comp. 7 | 1,000 | <0.1 | <0.1 | <0.1 | <0.1 | <0.1 | <0.1 | <0.1 | <0.1 |
|  | Comp. 8 | 1,180 | <0.1 | <0.1 | <0.1 | <0.1 | <0.1 | <0.1 | <0.1 | <0.1 |
|  | Comp. 9 | 1,400 | <0.1 | <0.1 | <0.1 | <0.1 | <0.1 | <0.1 | <0.1 | <0.1 |
|  | Comp. 10 | 2,000 | <0.1 | <0.1 | <0.1 | <0.1 | <0.1 | <0.1 | <0.1 | <0.1 |

As confirmed from Tables 2 and 3 above, when the xylylene diisocyanate composition was stored in a stainless steel container, the amount of metals eluted was greatly increased as the chlorine content in the composition was increased. However, when it was stored in a container coated with polyethylene, almost no metal was detected even if the chlorine content in the composition was increased.

Example 2

Preparation of an Optical Lens 520 g of each composition stored for 6 months in the above Test Example 1 as a xylylene diisocyanate composition, 479.3 g of 3,3'-thiobis[2-[(2-mercaptoethyl)thio]-1-propanethiol, 0.15 g of dibutyl tin dichloride as a curing catalyst, and 0.80 g of Zelec™ UN as an internal mold release agent were mixed uniformly to prepare a polymerizable composition.

The polymerizable composition was subjected to stirring in a nitrogen atmosphere at room temperature and a reduced pressure for 30 minutes to remove air bubbles, and it was filtered with a Teflon filter of 3 μm.

The filtered polymerizable composition was injected into a glass mold assembled with an adhesive tape using nitrogen pressure. The glass mold injected with the polymerizable composition was placed in a forced circulation oven, and the temperature was elevated from 25° C. to 120° C. at a rate of 5° C./min, followed by polymerization at 120° C. for 18 hours. Thereafter, the polymerized resin was further cured at 130° C. for 4 hours, and a lens was released from the glass mold to obtain each optical lens having a center thickness of about 1.2 mm.

Test Example 3

Evaluation of the Optical Lenses

The optical lenses produced in Example 2 were evaluated for the physical properties as shown in Table 4 below.

(1) Refractive Index and Abbe Number

The optical lenses were measured for refractive index and Abbe number at 20° C. using an Abbe refractometer DR-M4 model manufactured by Atago Co.

(2) Yellowness Index and Optical Transmittance

The optical lenses were measured for chromaticity coordinates x and y using a spectrophotometer CM-5 manufactured by Minolta Co., from which their yellow indices were calculated with Equation 1 below. Further, the transmittance at a wavelength of 550 nm was measured from the spectrum obtained using the same instrument.

$$YI=(234x+106y+106)/y \quad \text{[Equation 1]}$$

(3) Glass Transition Temperature (Tg)

The optical lenses were measured for glass transition temperature (Tg) with a thermal mechanical analyzer (TMA Q400, TA Instruments Co.) by a penetration method (load of 50 g, pin line of 0.5 mm φ, temperature elevation rate of 10° C./min).

(4) Stria 100 optical lenses were observed under a mercury lamp with naked eyes. The lenses having a nonuniform image were classified as having a stria, and the percentages thereof were calculated. As a result, if the percentage of the stria occurrence was 5% or less, it was evaluated as good, and if the percentage of the stria occurrence was 5% or more, it was evaluated as poor.

TABLE 4

|  |  | Chlorine (ppm) | Refractive index (nd) | Abbe number (ve) | Optical transmittance (%) | Tg (° C.) | Yellowness index (Y.I.) | Striae |
|---|---|---|---|---|---|---|---|---|
| m-XDI | Comp. 1 | 15 | Not measurable | Not measurable | 65 | 102 | 10 | Poor |
|  | Comp. 2 | 60 | 1.6633 | 25 | 87 | 102 | 12 | Poor |
|  | Comp. 3 | 100 | 1.6675 | 31 | 87 | 102 | 12 | Good |
|  | Comp. 4 | 300 | 1.6675 | 31 | 70 | 103 | 11 | Good |
|  | Comp. 5 | 530 | 1.6674 | 31 | 88 | 105 | 10 | Good |
|  | Comp. 6 | 750 | 1.6675 | 31 | 87 | 105 | 11 | Good |
|  | Comp. 7 | 1,000 | 1.6673 | 31 | 88 | 103 | 12 | Good |
|  | Comp. 8 | 1,180 | 1.6651 | 25 | 88 | 103 | 20 | Good |
|  | Comp. 9 | 1,400 | 1.6650 | 24 | 88 | 103 | 35 | Poor |
|  | Comp. 10 | 2,000 | 1.6630 | 26 | 50 | 63 | 50 | Poor |

As confirmed from Table 4 above, the lenses produced from the xylylene diisocyanate compositions having a chlorine content of 100 to 1,000 ppm even after storage for 6 months were excellent in all of the refractive index, Abbe number, transmittance, Tg, and yellowness index.

In contrast, the lenses produced from the other xylylene diisocyanate compositions having a chlorine content of less than 100 or greater than 1,000 ppm after storage for 6 months were poor at least one of the refractive index, Abbe number, transmittance, Tg, and yellowness index.

These results attribute to the fact that the content of chlorine greatly affects the reactivity of xylylene diisocyanate. Accordingly, if the chlorine content is less than 100 ppm, the storage stability of the composition is deteriorated due to the excessive reactivity, and the reaction becomes too rapid when it is used to produce a lens, resulting in nonuniform optical characteristics thereof. On the other hand, if the chlorine content exceeds 1,000 ppm, the retardation of the reactivity is excessive, so that the composition is unreacted or uncured when it is used to produce a lens, resulting in deterioration of optical characteristics thereof.

The invention claimed is:

1. A xylylene diisocyanate composition,
which has a chlorine content of 100 to 1,000 ppm and a content of NCO groups of 43 to 46% by weight, and
which comprises a chlorine-based storage stabilizer of the following Formula 1:

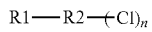

[Formula 1]

wherein
n is an integer from 1 to 3;
R1 is substituted or unsubstituted $C_{6-10}$ aryl; and
R2 is $C_{1-10}$ alkylene, and
the groups substituted in the aryl may be each independently selected from the group consisting of a halogen, hydroxy, and amino.

2. The xylylene diisocyanate composition of claim 1, wherein the chlorine-based storage stabilizer is benzotrichloride, benzyl chloride, or a mixture thereof.

3. The xylylene diisocyanate composition of claim 1, wherein when the xylylene diisocyanate composition is left at a temperature of 80° C. for 6 months, the amount of precipitates generated is 1% by weight or less based on the total weight of the composition.

4. The xylylene diisocyanate composition of claim 1, wherein when the xylylene diisocyanate composition is left at a temperature of 80° C. for 6 months, the change in the content of NCO groups contained in the composition is within 5% as compared with the initial content.

5. The xylylene diisocyanate composition of claim 1, wherein when the xylylene diisocyanate composition is sealed in a container that is not reactive with chlorine and left at a temperature of 80° C. for 6 months, the change in the content of the NCO groups contained in the composition is within 4% as compared with the initial content.

6. A process for preparing a xylylene diisocyanate composition, which comprises
obtaining a first composition containing xylylene diisocyanate from xylylenediamine by an isocyanate synthesis process; and
adding a chlorine-based storage stabilizer to the first composition to adjust the chlorine content in the composition to 100 to 1,000 ppm,
wherein the chlorine-based storage stabilizer is benzotrichloride, benzyl chloride, or a mixture thereof.

7. The process for preparing a xylylene diisocyanate composition of claim 6, wherein in the step of obtaining the first composition containing xylylene diisocyanate, xylylenediamine is reacted with phosgene, a halo $C_{1-10}$ alkyl chloroformate, or a halo di-$C_{1-10}$ alkyl carbonate to obtain a composition containing xylylene diisocyanate.

8. The process for preparing a xylylene diisocyanate composition of claim 6, further comprises, after adjusting the chlorine content in the composition, a step of subjecting the composition to heat distillation to remove excess chlorine-based compound present in the composition, to thereby adjust the chlorine content in the composition to 100 to 1,000 ppm.

9. A storage article of a xylylene diisocyanate composition, which comprises a xylylene diisocyanate composition of claim 1; and a container for containing the xylylene diisocyanate composition, wherein the regions of the container in contact with the xylylene diisocyanate composition are not reactive with chlorine.

10. The storage article of a xylylene diisocyanate composition of claim 9, wherein when the xylylene diisocyanate composition is sealed in the container and left at a temperature of 80° C. for 6 months, the change in the content of NCO groups contained in the composition is within 4% as compared with the initial content.

11. The storage article of a xylylene diisocyanate composition of claim 9, wherein the regions of the container in contact with the xylylene diisocyanate composition are made of a non-metal.

12. The storage article of a xylylene diisocyanate composition of claim 9, wherein the regions of the container in contact with the composition are coated with at least one selected from the group consisting of epoxy-based, polyethylene-based, fluorine-based, silicone-based, phenol-based, alkyd-based, polyester-based, acrylic-based, amino-based, vinyl-based, molybdenum-based, phosphate-based, and zinc-based coating agents.

13. The storage article of a xylylene diisocyanate composition of claim 9, which has a residual metal content in the xylylene diisocyanate composition of 1 ppm or less when the storage article is left at a temperature of 80° C. for 6 months.

14. A process for producing an optical lens, which comprises providing the xylylene diisocyanate composition of claim 1; and mixing the xylylene diisocyanate composition with a thiol and thermally curing the mixture in a mold.

15. The process for producing an optical lens of claim 14, wherein the optical lens has a yellowness index (YI) of 1 to 20 and a light transmittance of 85 to 99% at a wavelength of 550 nm.

16. The process for producing an optical lens of claim 14, wherein the optical lens has an Abbe number of 30 to 45 and a glass transition temperature of 95 to 120° C.

* * * * *